US012644840B2

(12) United States Patent
Pesala et al.

(10) Patent No.: US 12,644,840 B2
(45) Date of Patent: Jun. 2, 2026

(54) PATHOGENIC SUSCEPTIBILITY ASSESSMENT BASED ON AUTOFLUORESENCE

(71) Applicant: Adiuvo Diagnostics Private Limited, Siruseri Chennai (IN)

(72) Inventors: Bala Pesala, Siruseri Chennai (IN); Geethanjali Radhakrishnan, Siruseri Chennai (IN); John King, Siruseri Chennai (IN)

(73) Assignee: ADIUVO DIAGNOSTICS PRIVATE LIMITED, Siruseri Chennai (IN)

( * ) Notice: Subject to any disclaimer, the term of this patent is extended or adjusted under 35 U.S.C. 154(b) by 434 days.

(21) Appl. No.: 18/274,930

(22) PCT Filed: Jan. 31, 2022

(86) PCT No.: PCT/IN2022/050081
§ 371 (c)(1),
(2) Date: Jul. 28, 2023

(87) PCT Pub. No.: WO2022/162702
PCT Pub. Date: Aug. 4, 2022

(65) Prior Publication Data
US 2024/0053270 A1 Feb. 15, 2024

(30) Foreign Application Priority Data
Jan. 29, 2021 (IN) ............................. 202141004103

(51) Int. Cl.
*G01N 21/64* (2006.01)
*G01N 33/15* (2006.01)

(52) U.S. Cl.
CPC ......... *G01N 21/6486* (2013.01); *G01N 33/15* (2013.01)

(58) Field of Classification Search
CPC ........................... G01N 21/6486; G01N 33/15
See application file for complete search history.

(56) References Cited

U.S. PATENT DOCUMENTS

| | | | |
|---|---|---|---|
| 10,669,566 B2 | 6/2020 | Richards et al. | |
| 2018/0291419 A1* | 10/2018 | Richards ................... | C12Q 1/04 |
| 2018/0292324 A1* | 10/2018 | Verma ................ | G01N 21/6428 |

FOREIGN PATENT DOCUMENTS

| | | |
|---|---|---|
| WO | 2016011534 A1 | 1/2016 |

OTHER PUBLICATIONS

Graus et al., "Hyperspectral fluorescence microscopy detects autofluorescent factors that can be exploited as a diagnostic method for Candida species differentiation," Journal of Biomedical Optics, vol. 22, No. 1, pp. 016002-1-016002-6 (2017).

(Continued)

*Primary Examiner* — Michael L Hobbs
(74) *Attorney, Agent, or Firm* — Panitch Schwarze Belisario & Nadel LLP

(57) ABSTRACT

Examples of assessing susceptibility of a target pathogen based on autofluorescence, are described. In an example, a sample containing a target pathogen and a predefined concentration of a target drug may be obtained. Thereafter, autofluorescence features based on autofluorescence exhibited by the sample in response to the sample being subjected to excitation radiation, may be determined. Once the autofluorescence features are determined, they may be analyzed based on a susceptibility-detection model to determine susceptibility of the target pathogen with respect to the target drug. In an example, the susceptibility-detection model is trained based on a training autofluorescence features correlated with reference data, in which the reference data includes information pertaining to susceptibility or resistance of a reference pathogen with respect to a reference drug.

20 Claims, 13 Drawing Sheets

(56)         References Cited

OTHER PUBLICATIONS

Ju et al., "Deep Learning-Assisted Three-Dimensional Fluorescence Difference Spectroscopy for Identification and Semiquantification of Illicit Drugs in Biofluids," Anal. Chem., vol. 91, pp. 9343-9347 (2019).
International Search Report and Written Opinion issued May 11, 2022 in PCT/IN2022/050081.

* cited by examiner

400

402

406

408

410

404

3.5
3.0
2.5
2.0
1.5
1.0
0.5

0    1    2    3    4    5    6    7    8    9    10

500

OBTAINING REFERENCE DATA WHICH INCLUDES INFORMATION PERTAINING TO SUSCEPTIBILITY OR RESISTANCE OF A GIVEN PATHOGEN WITH RESPECT TO A PLURALITY OF DRUGS 502

↓

OBTAINING TRAINING AUTOFLUORESCENCE PARAMETERS FOR THE DIFFERENT PATHOGENS AND THEIR SUSCEPTIBLE OR RESISTANT DRUGS 504

↓

ASSOCIATING TRAINING AUTOFLUORESCENCE PARAMETERS MAY BE ASSOCIATED WITH THE REFERENCE DATA TO PROVIDE CORRELATED DATA 506

↓

TRAINING THE SUSCEPTIBILITY DETECTION MODEL BASED ON CORRELATED DATA 508

↓

IMPLEMENTING THE TRAINED SUSCEPTIBILITY DETECTION MODEL IN A SUSCEPTIBILITY ASSESSMENT SYSTEM 510

COLLECTING ONE OR MORE SAMPLES MAY BE COLLECTED FOR ANALYSIS 512

↓

SUBJECTING THE SAMPLE INCLUDING THE TARGET DRUG TO EXCITATION RADIATION 514

↓

DETECTING EXHIBITION OF THE AUTOFLUORESCENCE FROM THE RADIATED SAMPLE THROUGH A DETECTOR 516

↓

ANALYZING THE CAPTURED FLUORESCENCE DATA TO DETERMINE AUTOFLUORESCENCE FEATURES 518

↓

ANALYZING THE AUTOFLUORESCENCE PARAMETERS CORRESPONDING TO THE RADIATED SAMPLE BASED ON THE TRAINED SUSCEPTIBILITY DETECTION MODEL 520

↓

GENERATING A SUSCEPTIBILITY INDICATION BASED ON THE ANALYSIS OF THE AUTOFLUORESCENCE PARAMETERS 522

FIG. 5

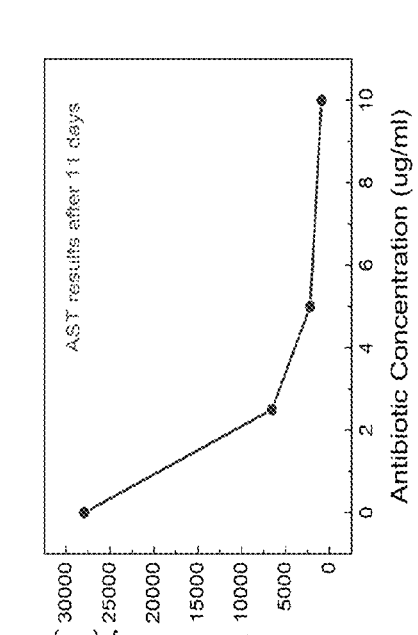
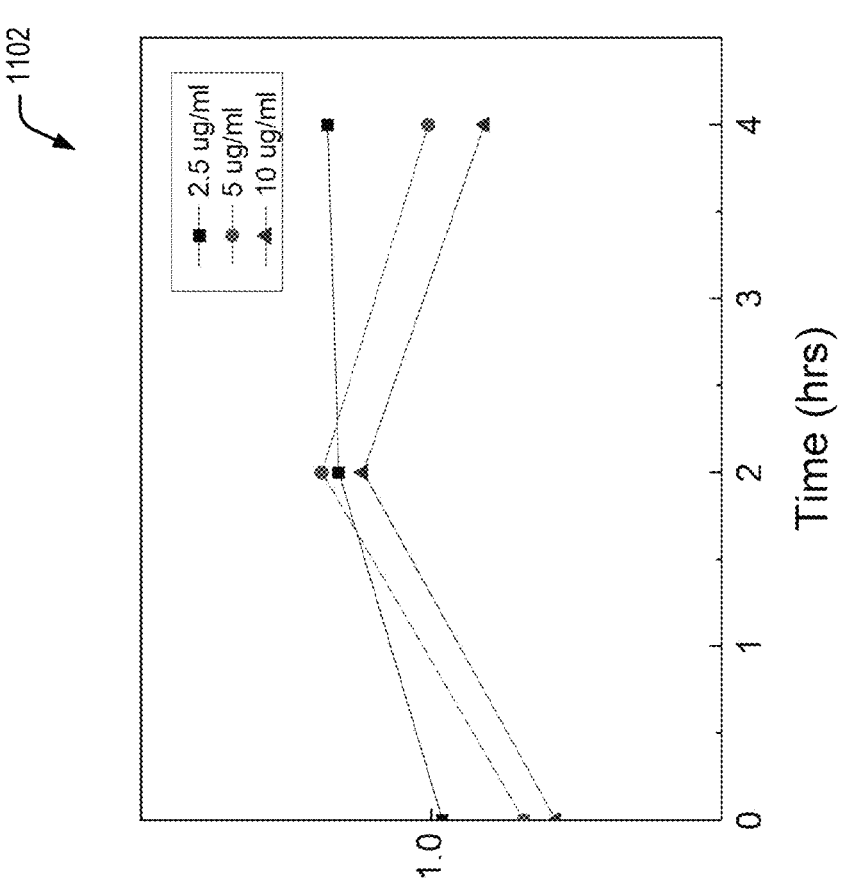
FIG. 11

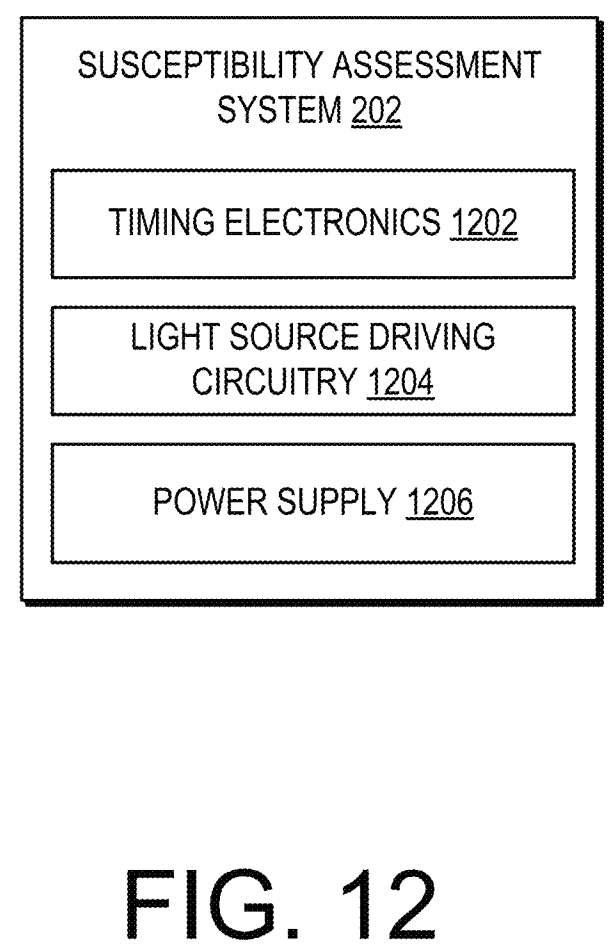

SUSCEPTIBILITY ASSESSMENT SYSTEM 202

TIMING ELECTRONICS 1202

LIGHT SOURCE DRIVING CIRCUITRY 1204

POWER SUPPLY 1206

FIG. 12

PATHOGENIC SUSCEPTIBILITY ASSESSMENT BASED ON AUTOFLUORESENCE

CROSS-REFERENCE TO RELATED APPLICATIONS

This application is a Section 371 of International Application No. PCT/IN2022/050081, filed Jan. 31, 2022, which was published in the English language on Aug. 4, 2022 under International Publication No. WO 2022/162702 A1, which claims priority under 35 U.S.C. § 119 (b) to Indian Application No. 202141004103, filed Jan. 29, 2021, the disclosures of which are incorporated herein by reference in their entireties.

TECHNICAL FIELD

The present subject matter relates in general to systems and methods for anti-microbial and anti-fungal testing, and in particular to approaches for rapid anti-microbial and anti-fungal testing using pathogen autofluorescence.

BACKGROUND

A key function of the clinical microbiology laboratory is to perform antimicrobial susceptibility testing (AST) on clinically significant isolates. Commercial systems for AST may be divided into automated, semiautomated, and manual. An automated testing system includes automated inoculation of Minimum Inhibitory Concentration (MIC) panels followed by computer-assisted incubation with reading, interpretation, and reporting functions that do not require manual intervention. As may be understood, MIC is the lowest concentration (represented in µg/mL) of an antibiotic that inhibits the growth of a given strain of bacteria. A semi-automated system comprises of manual or automated inoculation of panels and manual off-line incubation of panels. In such approaches, each panel is loaded into an automated reader, and computer-assisted reading and interpretive reporting of MICs is performed. Manual AST panels are inoculated and incubated manually, read visually by laboratory personnel, and the results are either recorded by hand or manually entered into a computer for interpretation and reporting. Each automated, semiautomated, or manual broth microdilution system provides a selection of AST panels with a fixed configuration of antimicrobial agents.

BRIEF DESCRIPTION OF DRAWINGS

The detailed description is described with reference to the accompanying figures. In the figures, the leftmost digit(s) of a reference number identifies the figure in which the reference number first appears. The same numbers are used throughout the drawings to reference like features and components.

FIG. 5 illustrates a method for training a susceptibility detection model and for assessing susceptibility of a target pathogen, based on a susceptibility detection model, as per an example.

FIGS. 10-11 demonstrate a graphical response for detecting the *Mycobacterium tuberculosis* in a sputum sample and antibiotic susceptibility testing, as per an example.

FIG. 12 demonstrate specific implementation of time dependent fluorescence parameters capture for antibiotic susceptibility testing, as per an example.

DETAILED DESCRIPTION

Figure 1:
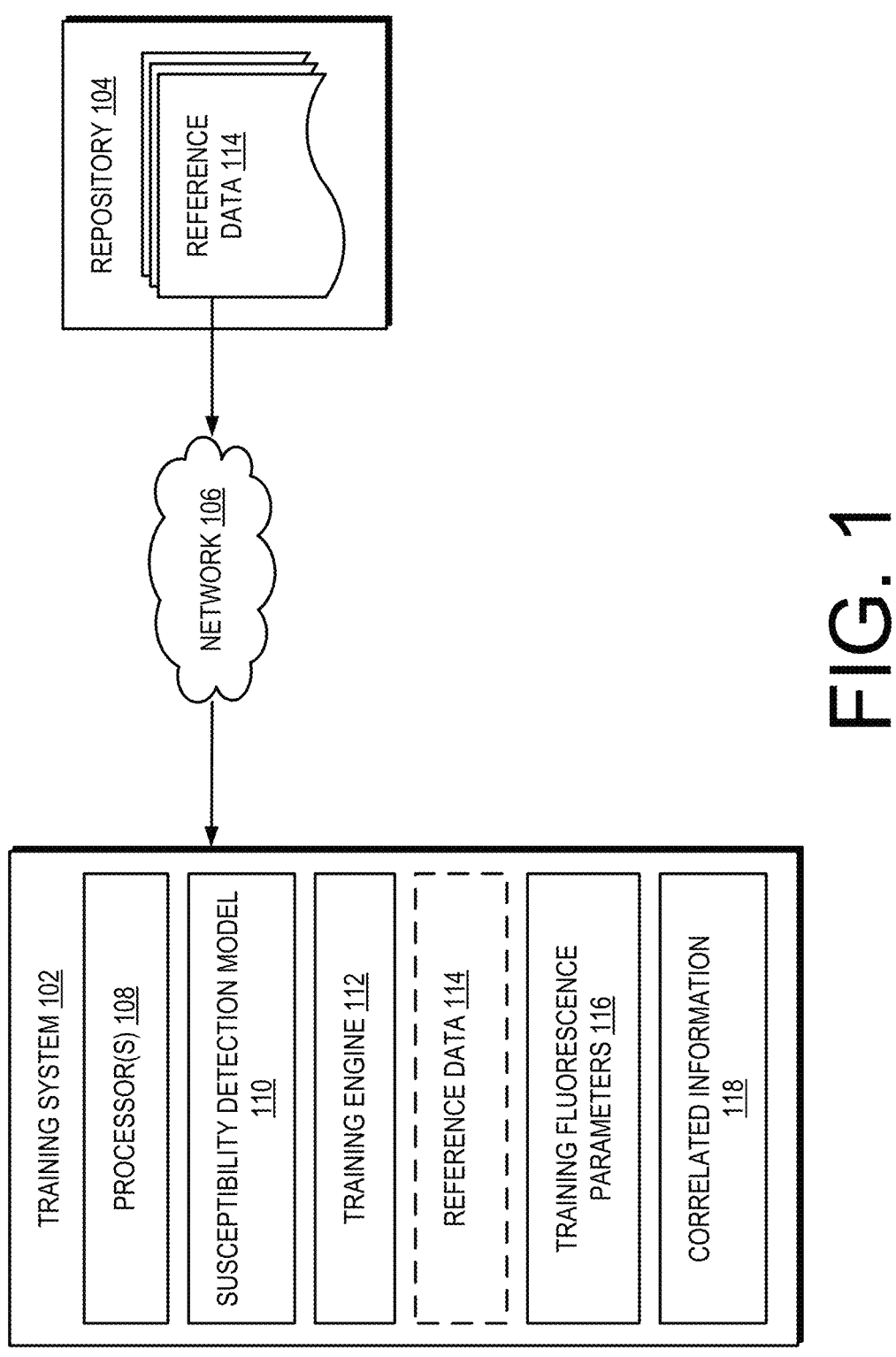
FIG. 1 depicts a schematic representation of a system for training a susceptibility detection model, as per an example.

Antimicrobial resistance (or AMR) has emerged as a global concern to public health causing many deaths, which is estimated to increase further with time. Antibiotic resistance has been increasingly detected with respect to a variety of conditions, examples of which include, but are not limited to, blood sepsis, skin and soft tissue infections (SSTIs), tuberculosis (TB), urinary tract infection (UTI), etc. Specific to SSTIs, antimicrobial-resistant bacteria may result in prolonged debility of the patient and increased healthcare costs. Identifying the causative agent and their susceptibility pattern is important in rational prescription of antimicrobials.

Conventional approaches, such as culture and micro broth dilution-based methods for AST detection are cumbersome. In culture and micro broth dilution-based methods, a sample of tissue bearing the pathogen may be drawn from a patient. The pathogen, using appropriate culture medium, may be grown, and identified using a variety of biochemical methods and the antibiotic susceptibility is analyzed for different types and concentration of antibiotics. This process is cumbersome requiring specialized microbiology facilities and takes 2-3 days for pathogens, such as bacteria, and may take over a week for fungi to be accurately identified and susceptibility to various antifungals assessed. Other methods for AST detection are known which have their own technical challenges. For example, there are several genotypic methods used for AST. However, such approaches typically require expensive instruments and reagents. In addition, genotypic methods do not work effectively for gram negative bacteria and also do not typically give minimum inhibitory concentration which is required to determine and adjust the antibiotic dosage.

Due to lack of rapid Antibiotic Susceptibility (AST) tests for identifying causative agents, generic antibiotics are prescribed. For example, carbapenem resistant *Pseudomonas aeruginosa*, methicillin-resistant *Staphylococcus aureus*, and the like have emerged as a serious threat with regards to SSTIs. Treatment of *Pseudomonas aeruginosa* and *Staphylococcus aureus* infections with antibiotics became often difficult because of the high potential of this pathogen to develop resistance, thus adding to its pathogenicity. To this end, approaches for quicker and more efficient assessment of antimicrobial susceptibility of pathogens are desired. This will aid in tackling existing and newly developing traits that emerge due to empirical therapy, misuse, and overuse of prevailing antimicrobial compounds. Rapid identification of pathogens also helps in improving patient outcome as subsequent treatment may be provided in a timely manner using appropriate targeted antimicrobial agents.

To address the foregoing technical challenges, examples described herein relate to approaches for assessing susceptibility of target pathogens, are described. Although certain examples of the present subject matter may be described in the context of certain bacteria, the approaches described therein may be applicable for any other pathogen, such as a virus, other bacteria, or fungi, without limiting the scope of the present subject matter. In an example, the assessment of susceptibility of target pathogens is based on the phenomenon of pathogen autofluorescence. Several pathogens, such as bacteria, fungi, and the like, exhibit characteristic autofluorescence when excited with different wavelengths in UV-A, UV-B, UV-C and visible range. Even NIR excitation using two photon absorption is used to excite autofluorescence biomarkers. As may be understood, autofluorescence occurs due to presence of biomolecules, such as Nicotinamide adenine dinucleotide (NADH) and variants, flavin, chitin, tryptophan, tyrosine, and porphyrin, etc. The present subject matter leverages on these autofluorescence biomarkers that are innately present in target pathogens for assessing susceptibility of such pathogens against a target drug, such as antimicrobial drugs. The present subject matter, thus, provides a direct phenotypic method for rapid drug susceptibility testing along with their minimum inhibitory concentration (MIC) that uses steady state autofluorescence measurements and/or fluorescence lifetime measurement of pathogens. The present subject matter provides rapid identification of pathogens while requiring less reagents and is cost effective. It may be noted that although the present subject matter has been described in the context of one or more pathogens exhibiting autofluorescence, the same approaches may be applicable in instances where certain appropriate exogenous fluorophores are utilized for pathogens. Exogenous fluorophores can target DNA, RNA, proteins, or biochemical markers present in the cells of the pathogens. Examples of such exogenous fluorophores include, but are not limited to, organic dyes, synthetic dyes, inorganic molecules such as quantum dots, or any combination thereof. Owing to the application of such exogenous fluorophores, the resulting pathogens may exhibit fluorescence, which may then be relied for assessing susceptibility of one or more target pathogens with respect to a target drug. Such approaches are further described below.

In an example, a patient sample (which may be infected with the pathogen) is subjected to a predefined concentration of a target drug. In addition, the patient sample with the pathogen may be subject to a stressor input. The stressor input is intended to enhance the response kinetics of the pathogen which in turn reduces time required for detection of the susceptibility of the pathogen under consideration. The stressor input may be an environmental condition, external stimulus or an event based to which the pathogen may be responsive to. In an example, the stressor may be a light input such as ultra-violet (UV), Blue, Red, or thermal stimulus such as heat, InfraRed (IR) or chemical stressor, such as alcohol, chlorine-based methods. Any other suitable stressor may be employed without deviating from the scope of the present subject matter. With the stressor input applied, the process may continue with the sample comprising pathogens being subjected to an excitation radiation. The excitation radiation may be either radiation having a single wavelength or may be a combination of a plurality of wavelengths. The sample in the presence of the target drug may be subjected to the excitation radiation for a predetermined duration, or for predetermined periodicity.

Owing to the excitation radiation, the pathogen sample may begin to exhibit autofluorescence. In an example, autofluorescence parameters may be determined. For example, images of the sample exhibiting autofluorescence may then be captured and analyzed to determine the autofluorescence parameters. In an example, the autofluorescence emission and time-dependent autofluorescence emission may be analyzed to determine one or more autofluorescence parameters. Such autofluorescence parameters may be understood as being expressed by one or more biomarkers which may be present in the pathogen. In an example, the autofluorescence parameters may include intensity, amplitude, or lifetime parameters. The autofluorescence parameters may thereafter processed using a machine learning-based detection model. The detection model may be initially trained. In an example, the detection model may be trained based on autofluorescence parameters. In the context of machine learning, training involves subjecting a machine learning model with training data. In an example, the training data may be based on autofluorescence parameters that may have been made obtained based on observing and capturing autofluorescence parameters of a pathogen interacting with a specific drug at various concentrations. Such autofluorescence parameters may be obtained for combinations of both pathogens which may be resistant to certain drugs and susceptible to other drugs. It may be noted that such parameters may be obtained based on fluorescence emissions which are caused due to exogenous fluorophores which may be added to the pathogens. Such approaches would also be within the scope of the present subject matter. In an example, machine and deep learning approaches can be directly used on the fluorescence decay curves to understand and assess the susceptibility. In yet another example, machine and deep learning techniques can be directly used on the obtained images. In an embodiment, deep learning techniques such as Convolutional Neural Networks (CNN) are used to obtain key spatial and spectral features from the images at various time intervals and these can be passed onto the recurrent neural networks or long-short term memory networks to directly assess the antibiotic susceptibility.

In an example, the above-described approaches may be implemented using a processor-based device. The processor-based device may be computing system or may be a compact, hand-held, or portable system that may be used for assessing susceptible of one or more pathogens with respect to a given target drug. In an example, the device may include components for providing excitation radiation and for capturing autofluorescence from the sample bearing the pathogens. These and other examples are further described in conjunction with the detailed figures.

The above examples are further described in conjunction with appended figures. It may be noted that the description and figures merely illustrate the principles of the present subject matter. It will thus be appreciated that various arrangements that embody the principles of the present subject matter, although not explicitly described or shown herein, may be devised from the description, and are included within its scope. Moreover, all statements herein reciting principles, aspects, and examples of the present subject matter, as well as specific examples thereof, are intended to encompass equivalents thereof. In the figures, the left-most digit(s) of a reference number identifies the figure in which the reference number first appears. The same numbers are used throughout the figures to reference like features and components.

As may be noted, unlike molecular profiling techniques or other conventional approaches to detect resistant strains, which are expensive and prone to errors due to continuous mutation of the bacteria, by using the present subject matter no specific bio-chemical markers needs to be added to the bacterial/fungal samples for AST determination and the AST is directly inferred from the real time bacterial response to a particular antibiotic drug, making this technique more direct and accurate. In addition, minimum inhibitory concentration can be directly inferred from phenotypic AST compared to genotypic AST. The present method also incorporates light (UV, blue, red etc.), chemical, heat-based stressors for enhancing the bacterial response when exposed to antibiotics. The fluorescence changes can be detected at a very early stage using chemometric, machine learning or deep learning techniques enabling rapid profiling of the bacteria into drug sensitive/resistant type under 2-5 hours. When compared to the existing methods, the present subject matter examines the autofluorescence emission changes when the pathogen encounters antibiotic stress which makes the testing more accurate, rapid, and cost effective.

FIG. 1 illustrates a training system 102 for training a susceptibility-detection model. The susceptibility-detection model, as will be explained subsequently, will be utilized for determining susceptibility of a given pathogen to one or more target drugs. The susceptibility-detection model is trained based on one or more autofluorescence parameters which may be obtained prior to the training of the susceptibility-detection model.

In an example, the training system 102 (referred to as the system 102) may be in communication with a predefined repository 104 through a network 106. The network 106 may be a private network or a public network and may be implemented as a wired network, a wireless network, or a combination of a wired and wireless network. The network 106 may also include a collection of individual networks, interconnected with each other and functioning as a single large network, such as the Internet. Examples of such individual networks include, but are not limited to, Global System for Mobile Communication (GSM) network, Universal Mobile Telecommunications System (UMTS) network, Personal Communications Service (PCS) network, Time Division Multiple Access (TDMA) network, Code Division Multiple Access (CDMA) network, Next Generation Network (NGN), Public Switched Telephone Network (PSTN), Long Term Evolution (LTE), and Integrated Services Digital Network (ISDN).

The system 102 may further include processor(s) 108 which may execute one or more computer executable instructions for training the susceptibility-detection model 110. The processor(s) 108 may be implemented as a single computing entity or may be implemented as a combination of multiple computing entities or processing units. The system 102 may further include a training engine 112. The training engine 112 may be implemented as a combination of hardware and programming, for example, programmable instructions to implement a variety of functionalities. In examples described herein, such combinations of hardware and programming may be implemented in several different ways. For example, the programming for the training engine 112 may be executable instructions, by the processor(s) 108. Such instructions may be stored on a non-transitory machine-readable storage medium which may be coupled either directly with the system 102 or indirectly (for example, through networked means). In an example, the training engine 112 may itself include a processing resource (not shown in FIG. 1), for example, either a single processor or a combination of multiple processors, to execute such instructions. In the present examples, a non-transitory machine-readable storage medium may store instructions, that when executed by the processing resource, implement training engine 112. In other examples, the training engine 112 may be implemented as electronic circuitry.

The system 102 may further include reference data 114 and training autofluorescence parameters 116. In operation, the system 102 may obtain reference data 114 from the repository 104. The repository 104 may be any implemented as any data storage repository which stores information pertaining the reference data 114. In an example, the reference data 114 may include information corresponding to either the susceptibility or resistivity of a reference pathogen with respect to a plurality of reference drugs. For example, the reference data 114 data may include that a given strain A of a reference bacterium may be resistant to a reference drug A', while another strain B of the same reference bacterium may be susceptible to a reference drug B'.

The reference data 114 may then be correlated with the training fluorescence parameters 116 (referred to as training parameters 116) corresponding to any given pathogen. To this end, the training parameters 116 may either be obtained in the form of autofluorescence intensity at various spectral bands. Such autofluorescence intensity may be captured by providing a sample with a reference pathogen to varying concentration of a given drug to which it may be susceptible. The sample may then be subjected to stressor inputs and then to excitation radiation pursuant to which it may exhibit autofluorescence. At this stage, data corresponding to the training parameters 116 may be determined through spectral analysis of the autofluorescence emissions and may be recorded. In another instance, an image of the autofluorescence emissions being exhibited may be captured and obtained, with the captured image being further analyzed for determining the training parameters 116. In this manner, training parameters 116 for a variety of pathogens subjected to different drugs to which they may be susceptible or resistant may be determined. In another example, the training parameters 116 may be obtained based on fluorescence emissions which are caused due to exogenous fluorophores which may be added to the pathogens. Such approaches would also be within the scope of the present subject matter.

The training parameters 116 (either based on exhibited autofluorescence or fluorescence) obtained in the manner as described above may be steady state fluorescence parameters or may be time dependent fluorescence parameters. The training parameters 116 may be steady state fluorescence if they correspond to fluorescence parameters that were observed or measured when the sample with the given drugs was subjected to excitation radiation for a continuous period of time. On the other hand, time dependent parameters may correspond to amplitude and lifetime parameters corresponding to time dependent fluorescence measurements. As may be understood, lifetime parameters may be determined by subjecting the sample to the excitation radiation for a specific time interval and then turned off. Pursuant to the same, the fluorescence decay curves, lifetimes, amplitude parameters may be observed. Owing to the absence of the excitation radiation, the emitted fluorescence will decrease with time which can be fitted with single or multiple exponentials. The fluorescence decay and lifetime parameters will differ for bacteria with and without antibiotic. The steady state and fluorescence lifetime parameters may also be used to first identify the pathogen. As would be further described in conjunction with later figures, the steady state and fluorescence lifetime may also be used to detect the presence or absence of the pathogens and then use the same parameters, such as the targets parameters 116 for ascertaining susceptibility of one or more target drugs. In this manner, training parameters 116 may be obtained. Training can also be done using machine and deep learning techniques on steady state fluorescence emission spectral response curves at various excitation wavelengths or fluorescence decay curves at various excitation and emission wavelengths instead of extracting specific parameters. Once the training parameters 116 are determined, they may be associated with the reference data 114 to provide the correlated information 118. The correlated information 118 thus obtained links the reference data 114, which includes information of pathogens and their susceptibility or resistance to one or more drugs, with the training parameters 116, obtained as explained above.

Returning to the present example, the training engine 112 may then train the susceptibility detection model 110 based on the correlated information 118. In an example, the susceptibility detection model 110 may be based on a number of classification, regression-based learning techniques, or deep learning techniques. An example of such a technique includes random forest. Other examples may also be utilized for implementing the susceptibility detection model 110, without deviating from the scope of the present subject matter. In an example, the susceptibility detection model 110 may be in the form of a classifier.

Once the susceptibility detection model 110 is trained, it may be utilized for determining whether the pathogen is resistant (or susceptible) to a target drug. To this end, the trained susceptibility detection model 110 may be implemented within a computing system for assessing drug resistance. The system may analyse the target strain to determine whether the target strain is resistant to the target drug.

Figure 2:
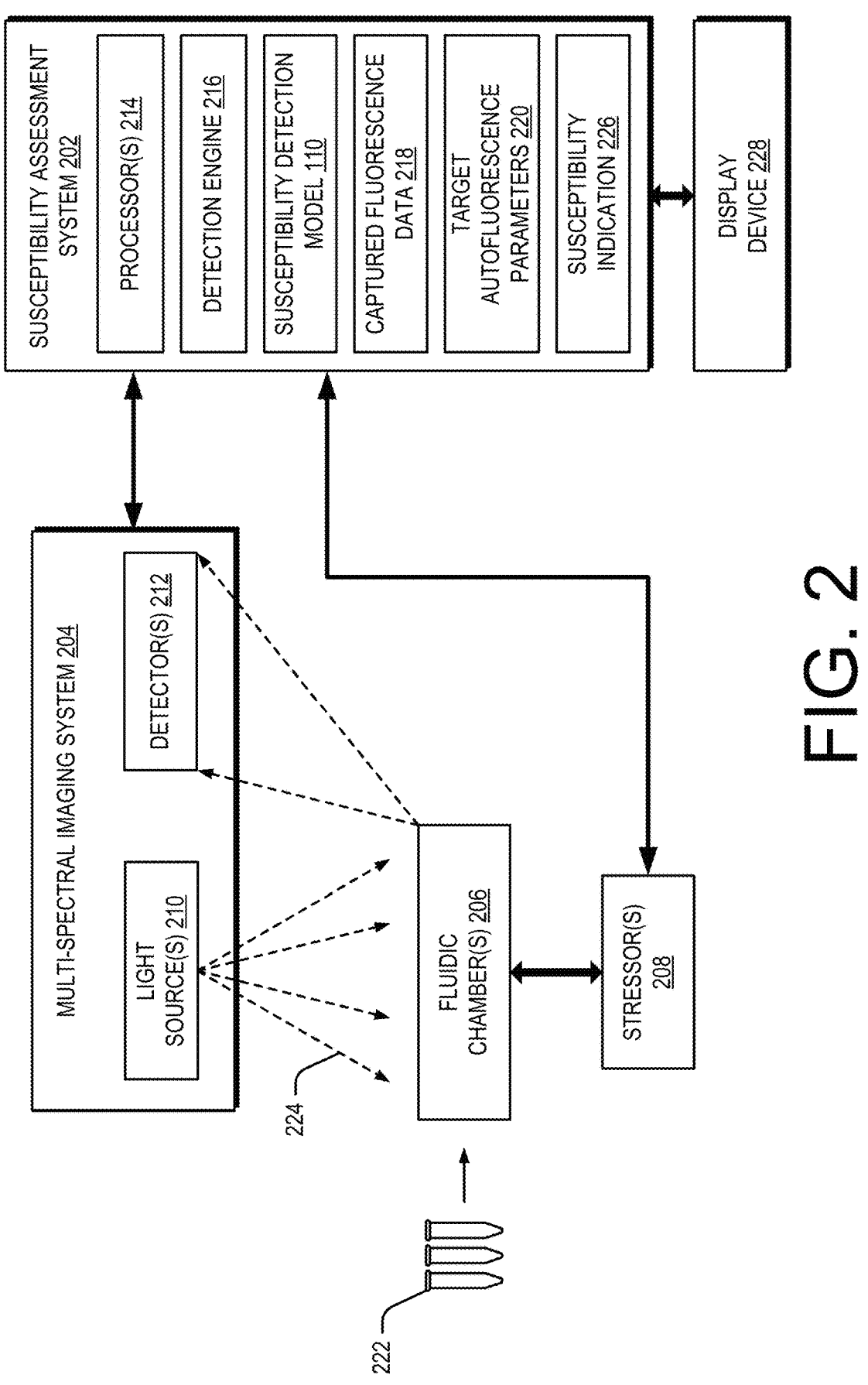
FIG. 2 illustrates a susceptibility assessment system for assessing susceptibility of a target pathogen with respect to a target drug, as per an example.

FIG. 2 depicts an environment 200 comprising a susceptibility assessment system 202 (hereinafter referred to as the assessment system 202). The assessment system 202 may be in communication with multi-spectral imaging system 204 (referred to as the imaging system 204). The imaging system 204 may be in communication with the assessment system 202 by way of a wired or a wireless communication or may be connected by way of a network (similar to the network 106). The assessment system 202 may be implemented within a clinical environment. Such a clinical environment may be an environment which may be testing one or more test samples acquired from one or more patients. The clinical environment may include any facility or institution implementing mechanisms for testing such samples for assessing susceptibility of pathogens which may be presented within the patient sample.

The imaging system 204 may be interacting with a fluidic chamber(s) 206 in which one or more patient samples may be loaded. The fluidic chamber(s) 206 may be exposed to one or more stressor(s) 208. The stressor(s) 208 may be a light such as ultra-violet (UV), Blue, Red or a thermal stressor such as heat, InfraRed (IR) or a chemical stressor such as alcohol, chlorine-based methods employed to enhance the pathogen response kinetics for reducing the detection time. In an example, the stressor(s) 208 may be coupled to the assessment system 202.

The system 204 comprises a plurality of light source(s) 210 to emit excitation radiation in a predetermined range of wavelengths. In an example, the excitation radiation from the light sources has a wavelength in the range from about 200 nm to 70 nm. In another example, the excitation can be in near-infrared wavelengths from 700 nm to 1000 nm to utilize two photon absorption. The plurality of light source(s) 210 can excite a sample comprising pathogens to the excitation radiation for a predetermined duration at a predetermined periodicity. The plurality of light source(s)

210 may be LEDs, lasers, and the like. Selection of light source(s) 210 is based on the auto fluorescent biomolecule or biomolecules present in the sample. The system 204 can be disposed above the sample to excite the pathogens in the sample.

The system 204 further comprises detector(s) 212 to capture the emitted auto fluorescence response inclusive of intensity and lifetime changes of amino acids, metabolic and infectious biomarkers and other cellular markers on addition with antibiotics. The fluorescence response may be captured as images of the samples exhibiting fluorescence or the fluorescence signals emitted by the sample once it has been subjected to excitation radiations as will be explained further. The detector(s) 212 may be an image capturing device, imaging sensors, or detectors examples of which include charge coupled device (CCD) detector, complementary metal oxide semiconductor (CMOS) detector, single-photon avalanche diode (SPAD)/Avalanche Photo detector (APD), photomultiplier tube (PMT) array, silicon photomultiplier (SiPM), Bolometer detector, CCD camera, CMOS camera and/or arrays of these detectors, and the like. Emission spectra can be captured in reflection or transmission geometry i.e., opposite to light source or reflection geometry i.e., same plane as the light source or any other angles of separation between the source and the detector.

In other examples, the detector(s) 212 may be a detector or a camera integrated with optimized emission filters to image the growth rate response exhibited by these autofluorescence biomarkers quantified using changes in autofluorescence intensity and lifetimes corresponding to various cellular biomarkers in real time to an antibiotic. In an example, the detector(s) 212 may also be a multispectral or hyperspectral camera provided with one or more customized filters. It may be noted that the present example of the detector(s) 212 is only indicative, with other examples also being possible. In addition, the detector(s) 212 may be integrated with other optical elements such as optical filter, polarizer for capturing fluorescence in various spectral bands and polarizations. The assessment system 202, as will be explained further, generates control instructions for activating the system 204. The system 204 when activated operates the light source(s) 210 and the detector(s) 212. The images captured by the detector(s) 212 may then be processed by the assessment system 202.

The assessment system 202 in turn may include processor(s) 214 (which may be similar to the processor(s) 108 as depicted in FIG. 1). The assessment system 202 may further include detection engine 216, the susceptibility detection model 110, captured fluorescence data 218, and target autofluorescence parameters 220 (referred to as the target parameters 220). As will be explained subsequently, the detection engine 216 may generate an indication which may indicate the type of pathogen and/or convey whether the pathogen under consideration is susceptible or resistant to the target drug. It may be noted that although the assessment system 202, the system 204, and fluidic chamber(s) 206 have been shown as separate logical blocks, they may be implemented within a single system, without limiting the scope of the claimed subject matter in any way. The different logical blocks have been shown as separate blocks for sake of explanation only and may be implemented as separate devices or systems or may be incorporated within a single system with one housing without deviating from the scope of the present subject matter.

In operation, one or more samples 222 may be collected and deposited in the fluidic chamber(s) 206. Prior to deposition in the fluidic chamber(s) 206, predefined concentrations of a target drug may be added to the samples 222 or coated. In an example, different concentration of the target drug may be added to different samples 222. In an example, samples 222 may include samples from different patients having different target pathogens or may be constituent of the same sample. The operation of the assessment system 202 is described with respect to a single sample 222 to which a predefined target drug is added. The same approaches would be applicable for various combinations of different pathogens and different concentration of target drugs, without deviating from the scope of the present subject matter. It is to be noted that it is the target pathogen (or pathogens, as the case may be) which are assessed to determine the susceptibility (or resistance) with respect to the target drug. In an example, the sample 222 may further include a predefined volume of growth media for aiding the growth and detection of the target pathogen.

Returning to the present example, the sample 222 with the target drug, may be deposited into the fluidic chamber(s) 206. Once the sample 222 deposited, the assessment system 202 may generate one or more control instructions to activate the system 204. The system 204 once activated may further activate the light source(s) 210. The light source(s) 210 when operational generate excitation radiation(s) 224 (as depicted in FIG. 2). The excitation radiation(s) 224 may include radiations of different wavelengths. In an example, the excitation radiation(s) 224 from the light source(s) 210 may have a wavelength in the range from about 200 nm to 600 nm. The excitation radiation(s) 224 thus emitted is to excite the sample 222 comprising the target pathogens for a predetermined duration at a predetermined periodicity. In an example, the sample 222 may be subjected to the excitation radiation(s) 224 for preset time interval before being turned off. In an example, the assessment system 202 may also generate control instructions for activating the stressor(s) 208. The stressor(s) 208 when activated are to enhance the response kinetics of the target pathogen. This in turn may reduce the time required for detection of the susceptibility (or resistance) of the target pathogen under consideration. It may be noted that although depicted as being communicatively coupled to the assessment system 202, the stressor(s) 208 may be manually and disjunctively operated from the assessment system 202.

When subjected to the excitation radiation(s) 224, the target pathogen in the sample 222 may exhibit autofluorescence. The autofluorescence may result in certain wavelengths of light being emitted by the sample 222. At this stage, the assessment system 202 may activate the detector(s) 212. The detector(s) 212 when activated may capture signals or images of the sample 222 exhibiting autofluorescence. In an example, the detector(s) 212 may capture the emitted auto fluorescence response. In an example, the autofluorescence response exhibited by the samples 222 may be based on the intensity of the autofluorescence radiation emitted by the sample 222. In another example, the autofluorescence response may be lifetime changes of metabolic and infectious biomarkers of the target pathogen in the sample 222 on addition with the target drugs. The target drugs may be antibiotics, antibacterial, antiviral, or antifungal drugs depending on the nature of the target pathogen being assessed.

As discussed previously, the fluorescence response may be detected by either capturing images of the samples 222 exhibiting fluorescence emissions or by detecting the fluorescence signals being emitted by the samples 222. The images or signals captured by the detector(s) 212 may be stored as captured fluorescence data 218. The captured fluorescence data 218 may be further analyzed by the detection engine 216 to determine one or more autofluorescence features expressed by biomarker present in the target pathogen in the sample 222. In an example autofluorescence features, e.g., intensity at various spectral bands, expressed may be stored as target parameters 220. The target parameters 220 may be determined based on a variety of signal processing techniques or image processing techniques to extract the fluorescence intensity and time dependent fluorescence parameters, such as amplitudes and lifetimes from the captured images. Such parameters are then made available as target parameters 220.

In an example, the excitation radiation(s) 224 may include white light radiation. In such instances, the system 202 may be used for assessing other attributes of the sample 222 radiated by the white light as excitation radiation(s) 224. For example, the system 202 may assess and analyze reflectance parameters, transmittance parameters, or combination thereof, for further processing and analysis by the detection engine 216. It may be noted that other attributes may also be considered without deviating from the scope of the present subject matter.

With the target parameters 220 thus determined, the detection engine 216 may process the obtained target parameters 220 based on the trained susceptibility detection model 110. As discussed in conjunction with FIG. 1, the susceptibility detection model 110 was trained based on autofluorescence training parameters 116. The susceptibility detection model 110 may now be used for identifying the patterns in the autofluorescence exhibited by the sample 222 (which was excited by the excitation radiation(s) 224). To this end, the detection engine 216 may analyze the target parameters 220 (which were obtained based on the exhibited autofluorescence by the sample 222) based on the susceptibility detection model 110. The analysis of the target parameters 220 may reveal whether the autofluorescence or fluorescence response is of the target pathogen which is resistant or susceptible to the target drug. In an example, the detection engine 216 may compare the target parameters 220 corresponding to the sample 222 are compared with weights and parameters of the detection model 110 which have been arrived at, based on the training process as discussed in conjunction with FIG. 1.

Such an assessment is based on the susceptibility detection model 110 which was trained on trained parameters corresponding to exhibited autofluorescence by target pathogens which were either resistant or susceptible to a given target drug.

Based on the assessment, the detection engine 216 may identify a given target pathogen and may also ascertain whether the sample 222 which bears the target pathogen is resistant or susceptible to the target drug provided therein. In an example, the detection engine 216 may generate a susceptibility indication 226. The susceptibility indication 226 may indicate whether the target pathogen in the sample 222 is susceptible or resistant to the target drug. In an example, the indication may also indicate what type the target pathogen is. The susceptibility indication 226 may be in the form of a message displayed as an alert provided on display device 228. Based on the susceptibility indication 226, any individual or technician within the environment 200 may conclude that the target pathogen under consideration is resistant or susceptible to the target drug which was added to the sample 222.

Figure 3:
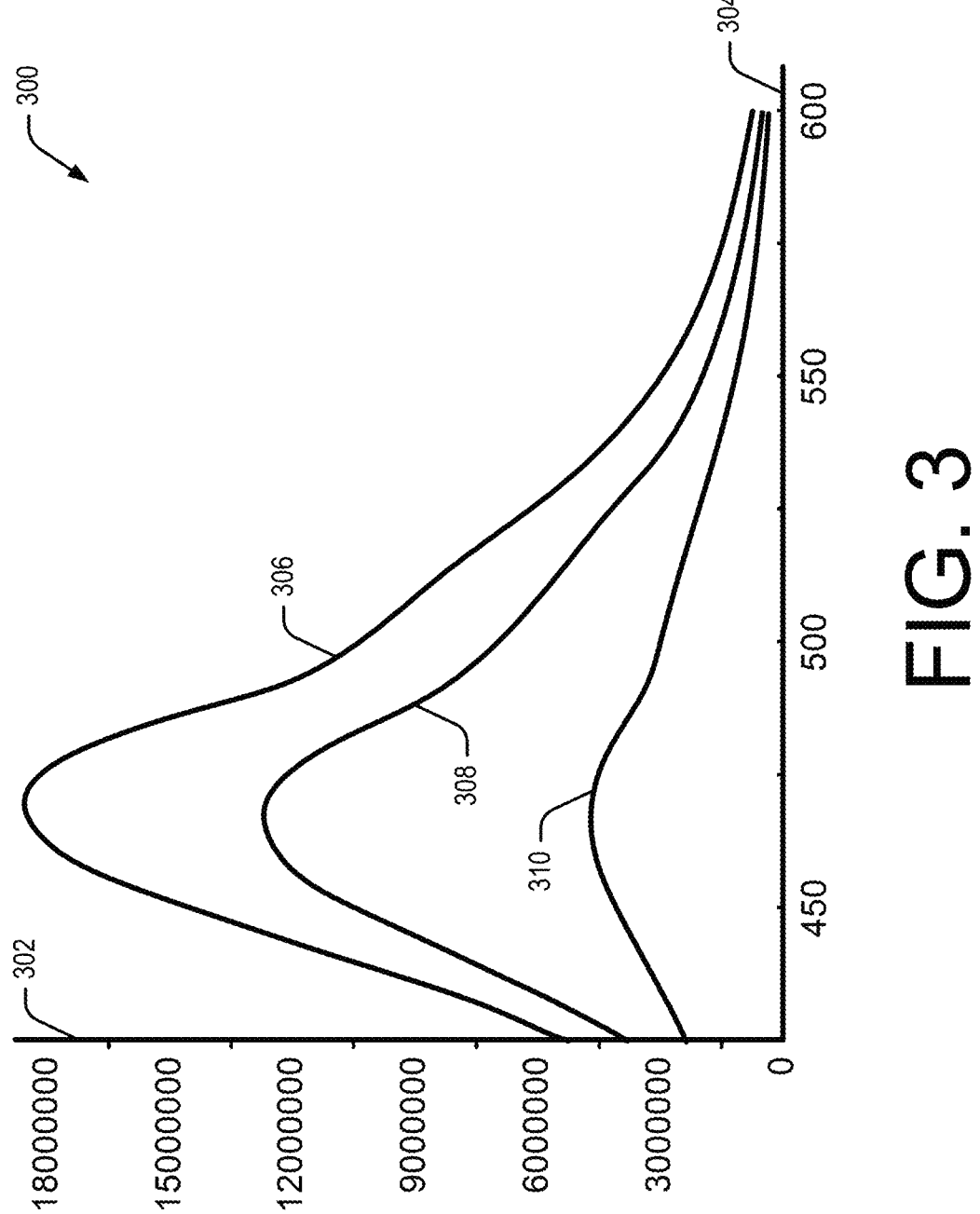
FIGS. 3-4 depicts intensity of autofluorescence of *Pseudomonas Aeruginosa* when exposed to different concentration of antibiotics, as per an example.
Figure 4:

FIGS. 3-4 provide graphs depicting fluorescence intensity as exhibited by a sample bearing the pathogen (e.g., the target pathogen). For example, the graph 300 depicts the variation of the fluorescence intensity against the emission wavelength. The graph 300 depicts an exemplary set-up in which resistance or susceptibility of *pseudomonas* bacteria is assessed. The graph 300 depicts the fluorescence intensity represented by the axis 302 (in AU) against the emission wavelength which is represented by the axis 304 (in nanometers or nm). The graph 300 further includes the variation depicted by the curve 306 which is to represent the variation of the pathogen's emission autofluorescence intensity (i.e., *pseudomonas* bacteria) without any target drug addition. Similarly, the curve 308 represents the variation in the fluorescence intensity of a resistant sample (*Pseudomonas aeruginosa* Resistant to meropenem). In the same way, the curve 310 represents the variation in the fluorescence intensity of a sensitive sample of *Pseudomonas aeruginosa* to meropenem drug. Each of the curves 306, 308, 310 provide a specific fluorescence response which is unique to a combination of the pathogen and the target drug. Based on the fluorescence response as depicted above, the detection engine 216 may, relying on the susceptibility detection model 110, identify whether target pathogen is susceptible or resistant to a target drug. FIG. 4 provides a graph 400 which depicts the variation of normalized intensity (fluorescence intensity normalized to fluorescence intensity at $0^{th}$ hour) (represented by axis 402) against the incubation, in hours, represented by the axis 404. The graphs 406, 408, 410, depict the variation of the normalized intensity for samples with only the pathogen, samples with a resistant *pseudomonas* bacterium, and sample with a susceptible *pseudomonas* bacterium, respectively. It may be noted that the graphs depicted in FIGS. 3-4 are only illustrative and correspond to one of the many other example pathogens, target drugs, and the combinations thereof, which may be assessed based on the approaches as described above.

FIG. 5 illustrates a method 500 to be implemented for assessing whether a target pathogen under consideration is resistant or susceptible to a target drug, as per an example of the present subject matter. Although the method 500 may be implemented in a variety of computing devices, for the ease of explanation, the present description of the example method 500 is provided in reference to the above-described training system 102 and the assessment system 202. The order in which the various method blocks of method 500 are described, is not intended to be construed as a limitation, and any number of the described method blocks may be combined in any order to implement the method 500, or an alternative method. It may also be noted that method 500 pertains to initially training a susceptibility detection model, such as the susceptibility detection model 110, and then subsequently determining whether a target strain is resistant to a given target drug. However, such steps may be performed separately at different instances without limiting the scope of the present subject matter in any manner.

Furthermore, the above-mentioned methods may be implemented in a suitable hardware, computer-readable instructions, or combination thereof. The steps of such methods may be performed by either a system under the instruction of machine executable instructions stored on a non-transitory computer readable medium or by dedicated hardware circuits, microcontrollers, or logic circuits. Herein, some examples are also intended to cover non-transitory computer readable medium, for example, digital data storage media, which are computer readable and encode computer-executable instructions, where said instructions perform some or all the steps of the above-mentioned methods.

At block 502, reference data which includes information pertaining to susceptibility or resistance of a given reference pathogen with respect to a plurality of reference drugs, may be obtained. For example, the training system 102 may obtain reference data 114 from the repository 104. In an example, the reference data 114 may include information corresponding to either the susceptibility or resistivity of a reference pathogen with respect to a plurality of reference drugs. For example, the reference data 114 data may include that a given strain A of a reference bacterium may be resistant to a reference drug A', while another strain B of the same reference bacterium may be susceptible to a reference drug B'.

At block 504, training or reference parameters may be obtained. For example, the training parameters 116 may either be obtained in the form of autofluorescence intensity at various spectral bands. Such autofluorescence intensity may be captured by subjecting a sample with a known reference pathogen to varying concentrations of a given reference drug to which it may be susceptible. The data corresponding to the training parameters 116 may be determined through spectral analysis and may be recorded. In another instance, an image of the autofluorescence being exhibited may be captured and obtained, with the captured image being further analyzed for determining the training parameters 116. In this manner, training parameters 116 for a variety of reference pathogens subjected to different drugs to which they may be susceptible or resistant, may be determined. In an example, the training parameters 116 may be obtained based on fluorescence emissions which are caused due to exogenous fluorophores which may be added to the pathogens. Such approaches would also be within the scope of the present subject matter. In an example, fluorescence parameters obtained from the detector or image sensor may be combined with reflectance and transmittance parameters at various excitation wavelengths for improving the accuracy of susceptibility estimation.

At block 506, the training parameters may be associated with the reference information, as obtained in the previous steps. For example, once the training parameters 116 are determined, the training engine 112 may associate the training parameters 116 with the reference data 114 to provide the correlated information 118. The correlated information 118 thus obtained links the reference data 114, which includes information of reference pathogens and their susceptibility or resistance to one or more drugs, with the training parameters 116.

At block 508, the correlated data may be used for training the susceptibility detection model. For example, the training engine 112 may then train the susceptibility detection model 110 based on the correlated information 118. In an example, the susceptibility detection model 110 may be based on a number of classifications, regression-based learning techniques, or deep learning techniques. An example of such a technique includes random forest. Other examples may also be utilized for implementing the susceptibility detection model 110, without deviating from the scope of the present subject matter. In an example, the susceptibility detection model 110 may be in the form of a classifier.

Once the susceptibility detection model 110 is trained, it may be utilized for determining whether a target pathogen is resistant (or susceptible) to a target drug. To this end, the trained susceptibility detection model 110 may be implemented within a computing system for assessing drug resistance. The system may analyze the target strain to determine whether the target strain is resistant to the target drug. This depicted in the method blocks that follow. It may be noted that the method blocks describing the assessment process may not follow immediately the preceding block but have been described in the present method for sake of explanation only.

Returning to the present method, at block 510, the trained susceptibility detection model may be implemented in a susceptibility assessment system. For example, the susceptibility detection model 110 once trained may be implemented within the assessment system 202. The assessment system 202 may be implemented within a clinical environment (e.g., the environment 200).

At block 512, one or more samples may be collected for analysis. For example, one or more samples 222 may be collected and deposited in the fluidic chamber(s) 206. Prior to deposition in the fluidic chamber(s) 206, predefined concentration of a target drug may be added to the samples 222. In an example, different concentration of the target drug may be added to different samples 222. In an example, samples 222 may include samples from different patients having different target pathogens or may be constituent of the same sample. The operation of the assessment system 202 is described with respect to a single sample 222 to which a predefined concentration of a target drug is added. The same approaches would be applicable for various combinations of different target pathogens and different concentrations of target drugs, without deviating from the scope of the present subject matter.

At block 514, the sample may be subjected to excitation radiation. For example, the assessment system 202 may cause the system 204, and in turn the light source(s) 210 to generate excitation radiation, such as the excitation radiation(s) 224. In an example, the excitation radiation(s) 224 may include radiations of different wavelengths, say in the range from about 200 nm to 600 nm. The excitation radiation(s) 224 thus emitted is to excite the sample 222 comprising target pathogens for a predetermined duration at a predetermined periodicity. In an example, the sample 222 may be subjected to the excitation radiation(s) 224 for preset time interval before being turned off. In an example, the assessment system 202 may also generate control instructions for activating the stressor(s) 208. The stressor(s) 208 when activated are to enhance the response kinetics of the target pathogen. This in turn may reduce the time required for detection of the susceptibility (or resistance) of the target pathogen under consideration. It may be noted that although depicted as being communicatively coupled to the assessment system 202, the stressor(s) 208 may be manually and disjunctively operated from the assessment system 202.

At block 516, exhibition of the autofluorescence from the radiated sample is detected through an image sensor or a detector. For example, when subjected to the excitation radiation(s) 224, the target pathogen in the sample 222 may exhibit autofluorescence. The autofluorescence may result in certain wavelengths of light being emitted by the sample 222. At this stage, the assessment system 202 may activate the detector(s) 212. The detector(s) 212 when activated may capture signals or images of the sample 222 exhibiting autofluorescence. In an example, the detector(s) 212 may capture the emitted autofluorescence response. In an example, the autofluorescence response exhibited by the samples 222 may be based on the intensity of the autofluorescence radiation emitted by the sample 222. In another example, the autofluorescence response may be lifetime parameter changes of metabolic and infectious biomarkers of the target pathogen in the sample 222 on addition with the target drugs.

At block 518, the signals or images captured may be stored and further analyzed to determine autofluorescence features corresponding to the autofluorescence exhibited by the radiated sample. For example, the images captured by the detector(s) 212 may be stored as captured fluorescence data 218. The captured fluorescence data 218 may be further analyzed by the detection engine 216 to determine one or more autofluorescence features expressed by biomarker present in the target pathogen in the sample 222. In an example autofluorescence features, e.g., intensity at various spectral bands, expressed may be stored as target parameters 220. The target parameters 220 may be determined based on a variety of signal processing techniques or image processing techniques to extract the fluorescence intensity and time dependent fluorescence parameters, such as amplitudes and lifetimes from the captured images. Such parameters are then made available as target parameters 220.

At block 520, the autofluorescence parameters corresponding to the radiated sample may be analyzed based on the trained susceptibility detection model. For example, the detection engine 216 may analyze the obtained target parameters 220 based on the trained susceptibility detection model 110. The analysis of the target parameters 220 may reveal whether the autofluorescence response is of a target pathogen which is resistant or susceptible to the target drug. In an example, the detection engine 216 may compare the target parameters 220 corresponding to the sample 222 are compared with weights and parameters of the At block 522, a susceptibility indication may be generated based on the analysis of the autofluorescence parameters. For example, based on the assessment, the detection engine 216 may ascertain whether the sample 222 which bears the target pathogen is resistant or susceptible to the target drug provided therein. In an example, the detection engine 216 may generate a susceptibility indication 226. The susceptibility indication 226 may indicate whether the target pathogen in the sample 222 is susceptible or resistant to the target drug. The susceptibility indication 226 may be in the form of a message displayed as an alert provided on display device 228. Based on the susceptibility indication 226, any individual or technician within the environment 200 may conclude that the target pathogen under consideration is resistant or susceptible to the target drug which was added to the sample 222.

Figures 6A, 6B:
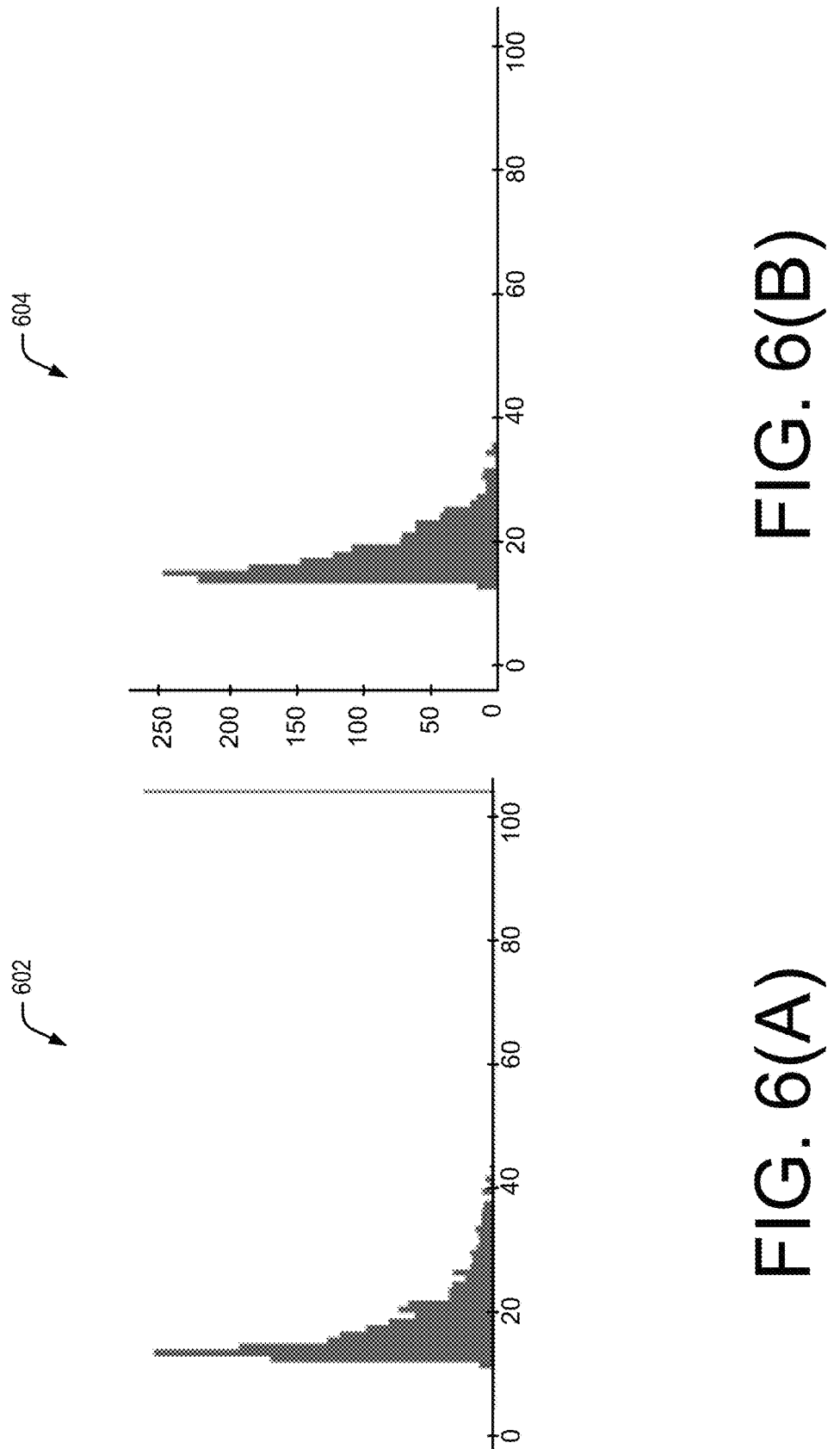
FIG. 6 illustrates time dependent autofluorescence results of a target pathogen with respect to a target drug to determine antibiotic susceptibility testing in an hour, as per an example.

FIG. 6(A) illustrates the fluorescence lifetime parameter changes when the bacterial sample is exposed to antibiotics, in accordance with an implementation of the present subject matter. As depicted in FIG. 6(A), the graph 602 depicts, in an example, time dependent fluorescence response of *Pseudomonas aeruginosa* subjected to excitation radiation (such as the excitation radiation(s) 224) of 395 nm and with long pass emission filter (>450 nm). In an example, the graph 602 may be depicted based on the following equations which may represent the extracted amplitudes and lifetime parameters:

$$R(t) = 0.66 * e^{\frac{t}{1.1}} + 0.34 * e^{\frac{t}{6.94}} \qquad \text{(Equation 1)}$$

FIG. 6(B) on the other hand illustrates the fluorescence lifetime parameter changes when the bacterial sample is exposed to antibiotics or a specific target drug, in accordance with an implementation of the present subject matter. The graph 604 in FIG. 6(B) depicts Time dependent fluorescence response change of *Pseudomonas aeruginosa* when subjected to excitation radiation (such as the excitation radiation(s) 224) of 395 nm and long pass emission filter (>450 nm). In the present example, the pathogenic sample under consideration is exposed to Meropenem antibiotic for a period of 1 hour. The response is captured in graph 604. In an example, the extracted amplitudes and lifetimes may be represented by the following equation:

$$R(t) = 0.64 * e\frac{t}{0.66} + 0.36 * e\frac{t}{6.07} \qquad \text{(Equation 2)}$$

Equation 2 as depicted above clearly demonstrates that upon exposure to antibiotic the fluorescence lifetime response changes which can help differentiate between susceptible and resistant strain. As would be appreciated, using the approaches as discussed above in conjunction with assessment system 202 and the method 500, various auto-fluorescence and fluorescence features expressed by bio-marker present in or added to the pathogen may be extracted based on captured digital signals or images and may be compared with key features extracted from the captured signals or images against a reference trained signals or images employing a deep neural network for rapid anti-microbial and anti-fungal testing. It is again iterated that the present depiction is in relation to one of the many other possible examples and is not meant to limit the scope of the claimed subject matter in any way.

Figure 7B:
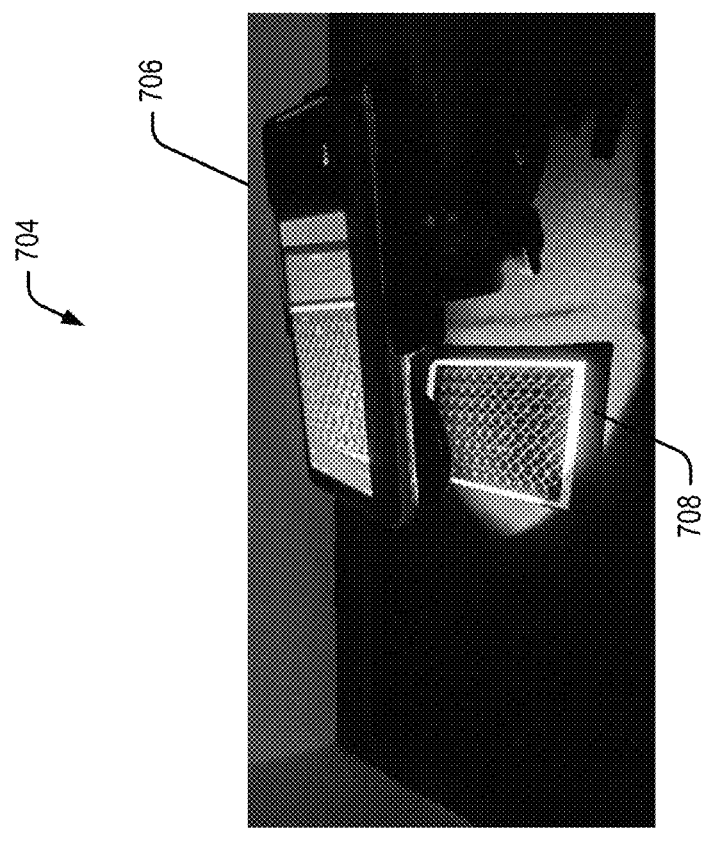
FIGS. 7-9 illustrate the device and results for antibiotic susceptibility testing of *Pseudomonas Aeruginosa* when exposed to antibiotics, as per an example.
Figure 7A:
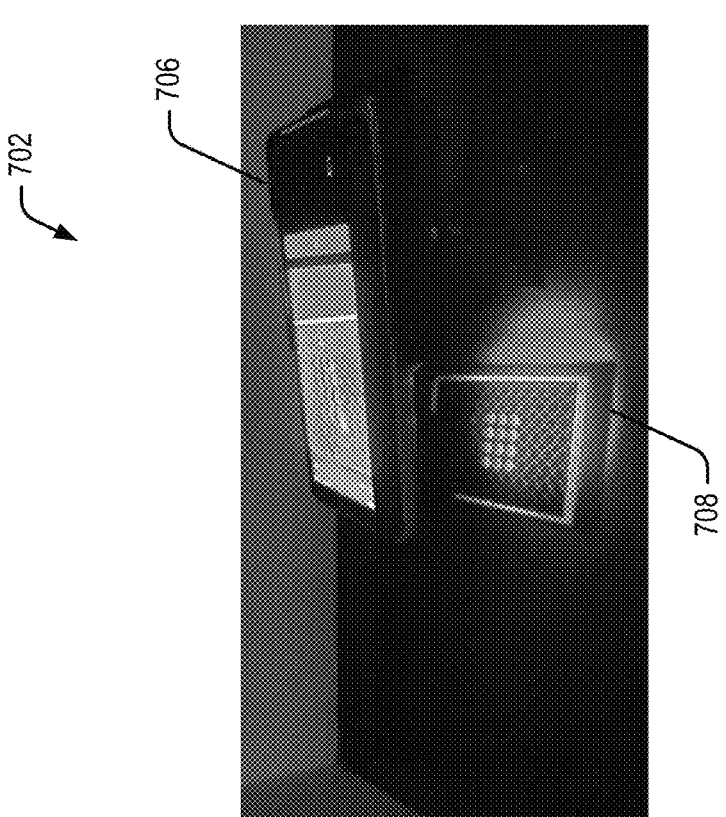

FIGS. 7(A)-(B) provides images 702, 704 depicting an experimental set-up comprising an imaging system 706 (such as the multi-spectral imaging system 204). As may be observed, the detector(s) 212 of the system 706 are to capture an image of a '96-well plate' (e.g., well plates 708 of the fluidic chamber(s) 206) each having a target drug of varying concentrations along with resistant and sensitive samples containing *Pseudomonas aeruginosa*. The detector(s) 212 may include CMOS sensors. In the example as depicted, well plates as depicted the fluidic chamber(s) 206 are radiated with the excitation radiation(s) 224. In an example, the excitation radiation(s) 224 which is utilized is having excitation wavelength in the range of about 365 nm to about 395 nm (as depicted in image 702). In response to the excitation radiation(s) 224 provided by the system 704, the samples within the well plate exhibit fluorescence emission. In the present example, the wavelengths of the emission fluorescence may be in the three spectral ranges, with the first range being about 460 nm to about 490 nm, the second range being about 515 nm to about 545 nm, and the third range being about 600 nm to about 650 nm.

Figures 8A, 8B:
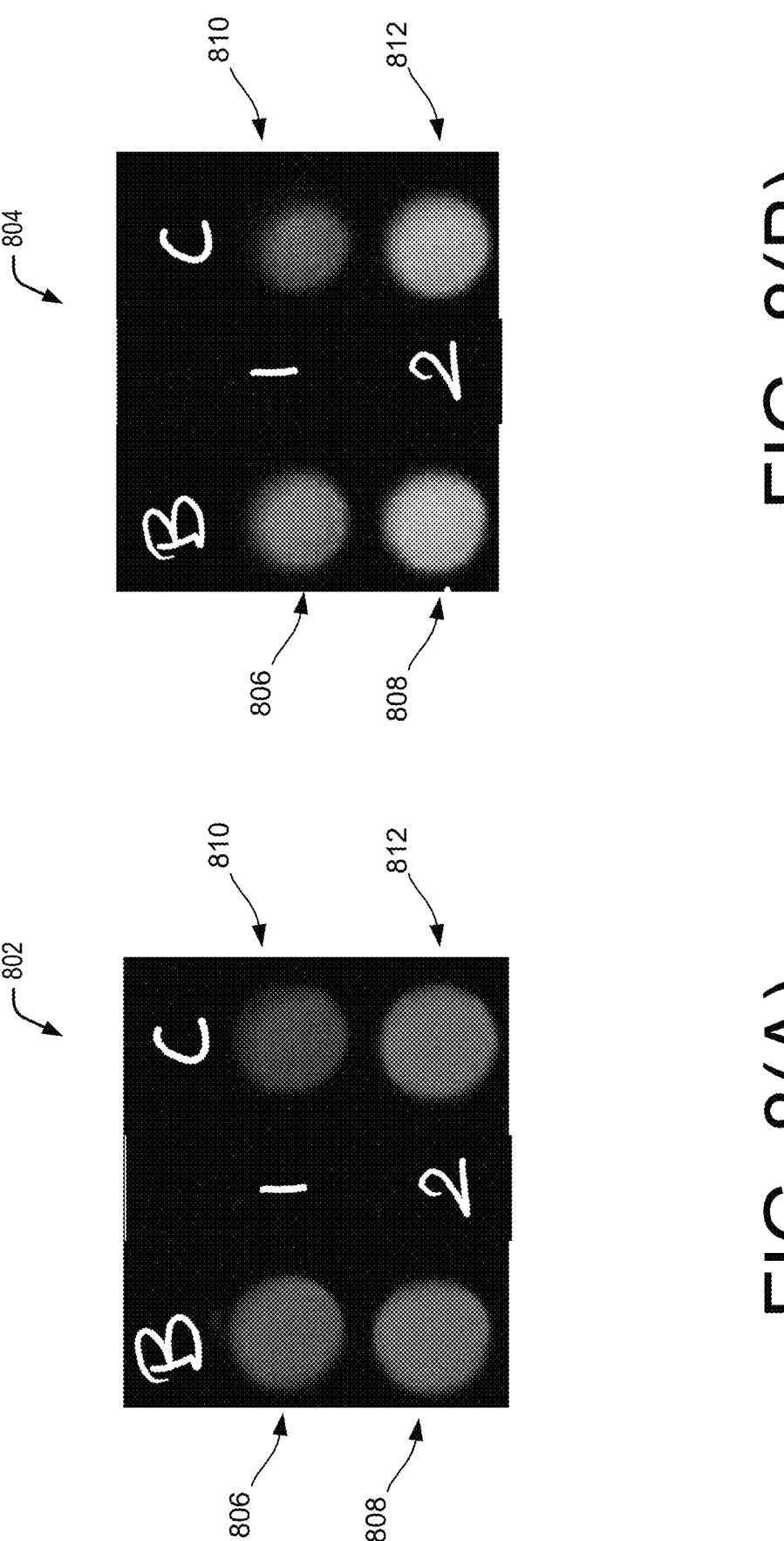

FIG. 8 provides images 802, 804 captured using the system 706 at $0^{th}$ hour and $4^{th}$ hour. The image 802 depict a first well 806 (B1), second well 808 (B2), third well 810 (C1), fourth well 812 (C2). The first well 806 corresponds to *Pseudomonas aeruginosa* sensitive strain, the second well 808 corresponds to *Pseudomonas aeruginosa* resistant strain which serves as control. Continuing further, the third well 810 corresponds to *Pseudomonas aeruginosa* sensitive strain which has been added with 4 µg/ml concentration of meropenem drug (Minimum Inhibitory Concentration (MIC) Value), and fourth well 812 corresponds to *Pseudomonas aeruginosa* resistant strain added to 4 µg/ml concentration of meropenem drug (MIC Value). The different images 802, 802 depict the varying fluorescence intensities exhibited by the sample after a certain period of time has elapsed.

Figure 9:
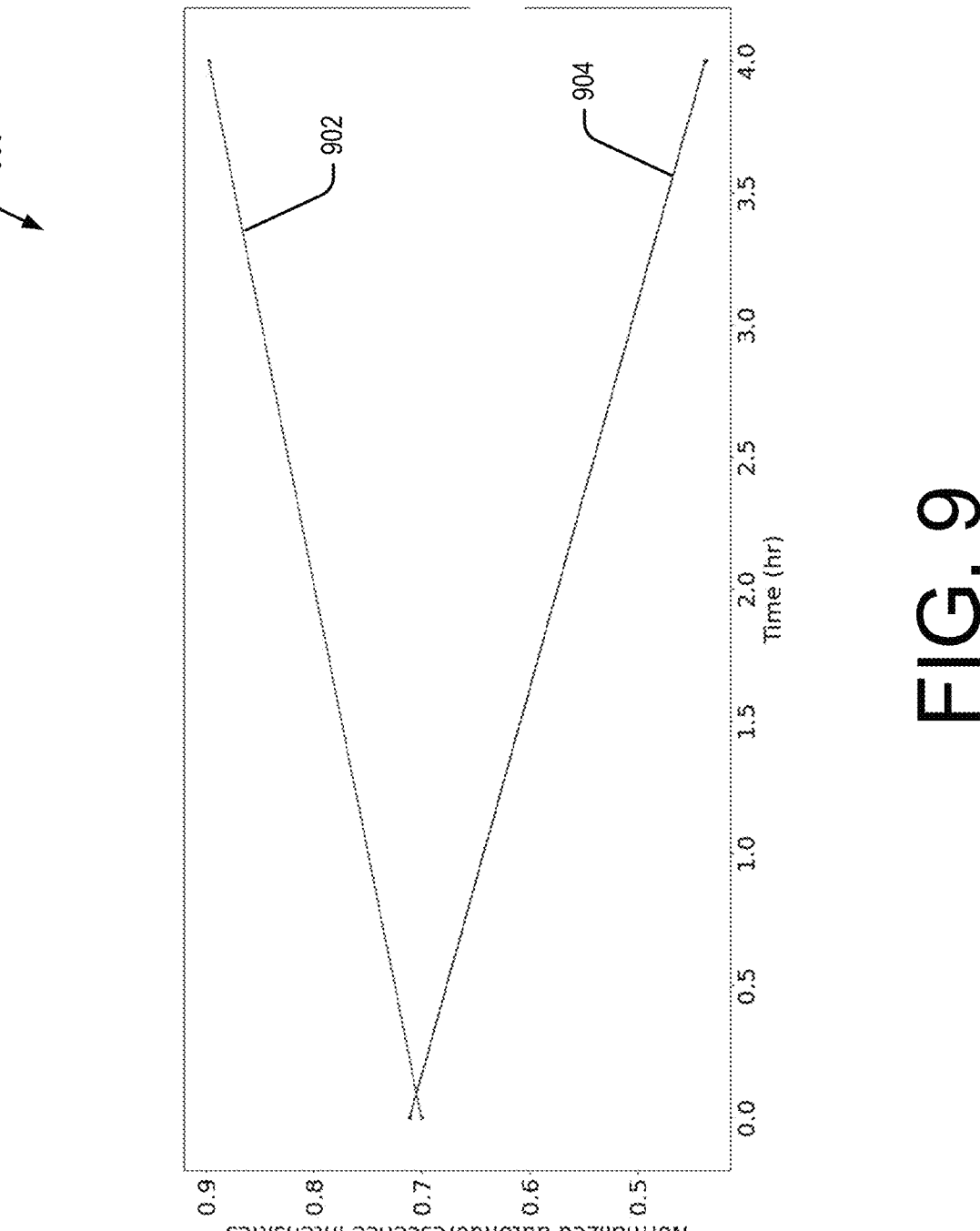

For the experimental set-up as exemplified in conjunction with FIGS. 7-8, the changes in the fluorescence intensity are depicted in graph 900 illustrated in FIG. 9. The graph 900 depicts the change in the fluorescence intensity from $0^{th}$ hour to $4^{th}$ hour between resistant strain (depicted by line 902) and sensitive strain of *Pseudomonas aeruginosa* (depicted by line 904). In an example, the graph 900 is obtained by calculating the normalized fluorescence intensity (fluorescence intensity of pathogen treated with antibiotic vs. fluorescence intensity of pathogen without antibiotic treatment) determined based on the images (such as the images 802, 804) captured by the detector(s) 212 within the system 706.

Figure 10:
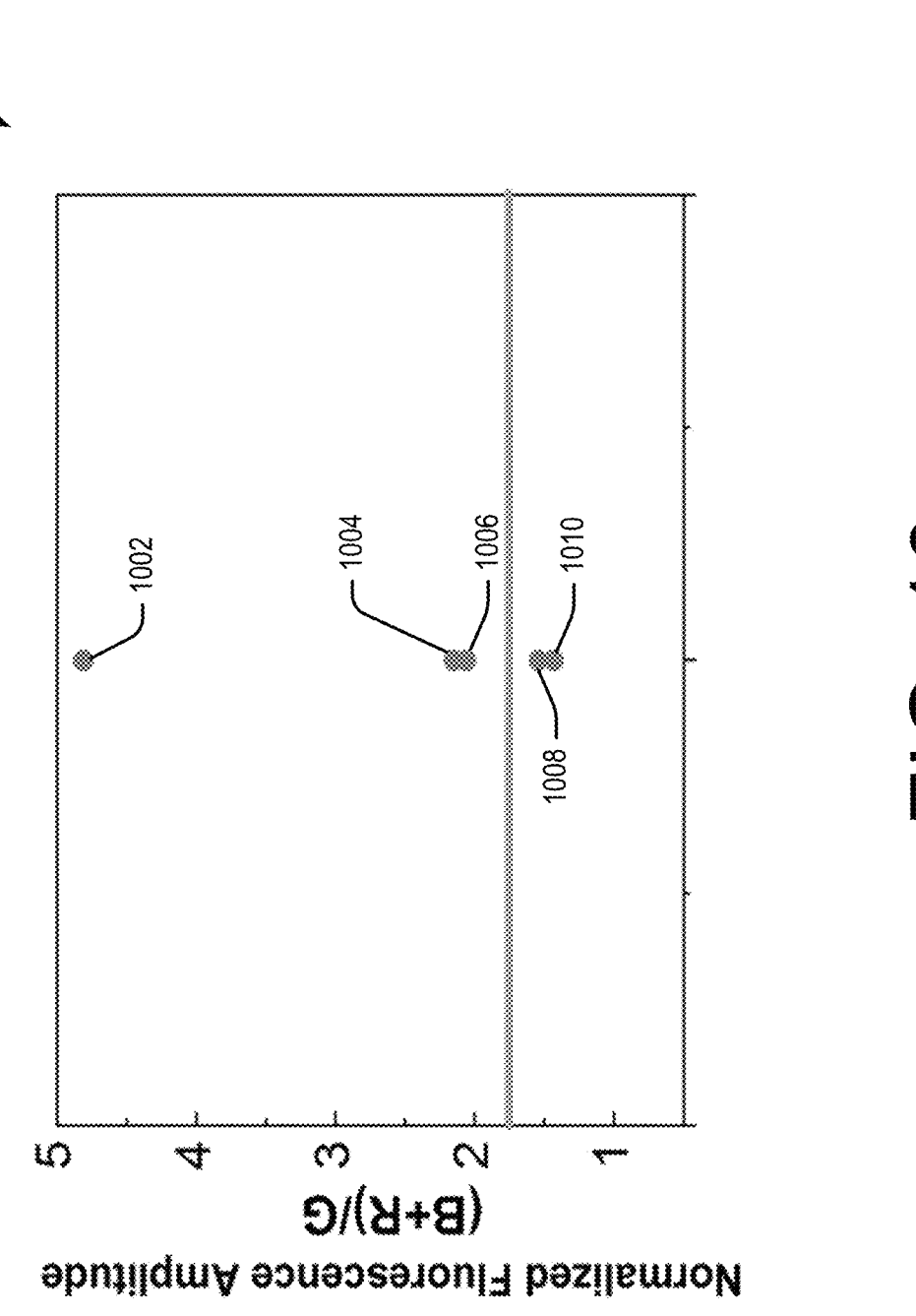

The above-mentioned approaches may also be used for determining presence of one or more pathogens within a sample. For example, images of exhibited fluorescence may be obtained by the detector(s) 212 of the system 204 for a certain sample and may be analyzed. Based on recorded normalized fluorescence amplitudes, a determination may be to ascertain whether a given patient sample includes a specific pathogen or not. FIG. 10 depicts a graph 1000 depicting recorded normalized fluorescence amplitudes recorded for a sputum sample. In the current example, the detector(s) 212 of the system 204 may capture the images of the sputum sample exhibiting the fluorescence. In the present example, the detector(s) 212 integrated with optical filters capture the exhibited fluorescence at three wavelength bands, with the first band being between 465 nm to 495 nm (depicted by B), the second band being between 515 nm to 545 nm (depicted by G), and the third band being 600 nm to 650 nm (depicted by R). For each of the above-mentioned band, the average intensities values may be calculated.

Thereafter, a threshold value may be set for the present assessment. In the present example, a threshold value of 1.7 is established to separate negative and positive samples for *Mycobacterium tuberculosis*. The threshold value may be selected based on a number of factors, for example, distribution of the normalized fluorescence intensity. In an example, the following formula was used to obtain decision threshold between *mycobacterium* positive and negative samples:

$$\text{Normalized fluorescence Intensity}=(B+R)/G \qquad \text{(Equation 3)}$$

In the present example, 5 sputum samples were measured using the system 204. The said samples, 2 samples were sputum sample without bacteria, 3 sputum samples are positive with *Mycobacterium tuberculosis*. The samples for which the evaluated normalized fluorescence amplitudes are greater than the threshold value may be elected as those samples in which the *mycobacterium* may be considered as present. In this example, normalized fluorescence intensity values 1002, 1004, 1006 would be corresponding to samples having *mycobacterium*, as opposed to values 1008 and 1010 which lie below the threshold value and hence would correspond to samples which are devoid of *mycobacterium*.

FIG. 11 relates to another example of using autofluorescence to assess susceptibility patterns from a sputum sample whose MIC is above 3 µg/mL, as depicted in graphs 1102 and 1104. In the present example, post identification of sputum samples positive of *Mycobacterium tuberculosis* (as explained with respect to FIG. 10) were further analyzed for susceptibility patterns. In this example, kanamycin as a target drug was added at different concentration 2.5 µg/mL, 5 µg/mL, 10 µg/mL. The graph 1102 is characterized by the x-axis representing intensity readings measured at $0^{th}$ hour, $2^{nd}$ hour, $4^{th}$ hour, with the y-axis representing fluorescence intensity (in arbitrary units or a.u). As may be seen, the graph clearly shows decrease in autofluorescence intensity being indicated above MIC 3 µg/mL. The graph 1104 on the other hand depicts the graph plotted for sputum sample added with various concentrations of kanamycin drug, for up to 11 days.

As explained previously, the susceptibility assessment system 202 and the multi-spectral imaging system 204 may be used for assessing susceptibility of a one or more pathogens for a target drug. The operation of the susceptibility assessment system 202 and the multi-spectral imaging system 204 has been explained with respect to a number of logical blocks as depicted in FIG. 2. These systems may be implemented in any way to achieve the described functions as explained above. In an example, the multi-spectral imaging system 204 may be implemented using a variety of functional, logical, electrical and electronic components which have not been indicated in FIG. 2. Such components may form the electronic circuitry within such systems or may aid in performing certain functions. For example, the system 204 (in addition to the logical blocks depicted in FIG. 2) may include timing electronics 1202 which will amongst other functions may coordinate the functions of the different components of the system 204. Continuing further, the system 204 may further include light source driving circuit 1204. The light source driving circuit 1204 may perform one or more control functions of other circuits or components, such as the light source(s) 210 and the detector(s) 212, of the system 204. Although not depicted, the system 204 may further include other driving circuits for controlling yet other components of the system 204. The system 204 may be powered through a power supply 1206, which may be used for powering the components and circuitry of the system 204 based on power drawn from an electric current source. The power supply 1206 may be implemented within the system 204 or may be present as an external element coupled to the system 204. Any other components or modules may also be present without deviating from the scope of the present subject matter.

Figure 13:
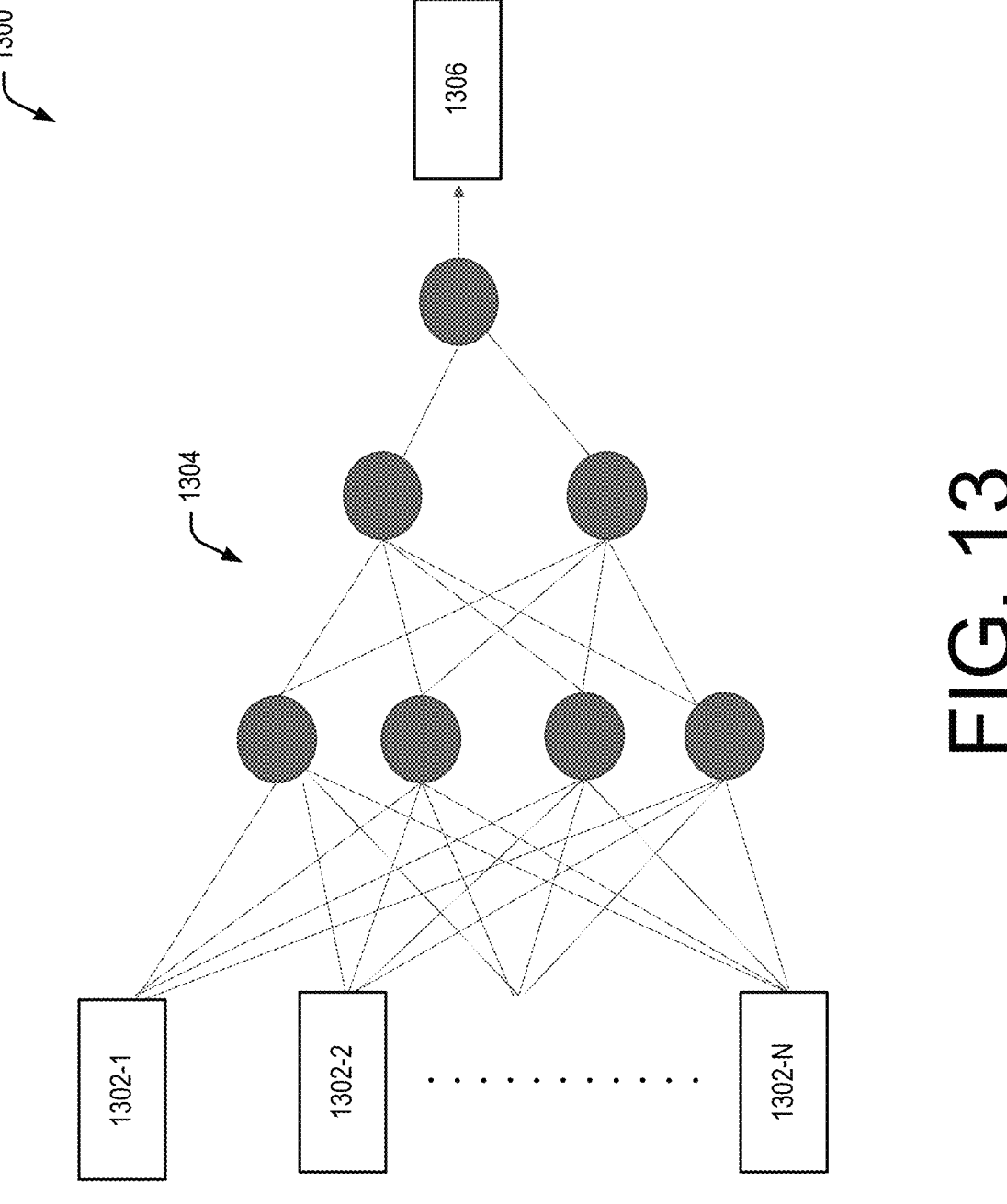
FIG. 13 depicts an example approach for training a neural network based on fluorescence parameters for antibiotic susceptibility testing, as per an example.

FIG. 13 depicts an example approach for training a neural network 1300 based on fluorescence parameters for antibiotic susceptibility testing, as per an example. The fluorescence parameters may include steady state fluorescence parameters and time dependent parameters. The neural network 1300 may include a plurality of input nodes 1302-1, 2, . . . , N (collectively referred to as nodes 1302) which comprise an input layer. In an example, the nodes 1302 may comprise fluorescence intensities, fluorescence lifetime parameters, or combinations thereof. The input nodes 1302 are coupled to the underlaying hidden layers 1304 defining the neural network 1300. The hidden layers 1304 may include, in one example, various weights or parametric values which are defined during the training phase, based on the training data provided through one or more of the input nodes 1302. The neural network 1300 may then comprise an output node 1306 which then represent or provide an indication conveying either the resistance or susceptibility of one or more target pathogens with respect to the target drugs. It may be noted that the depiction of the neural network 1300 is only by way of example and it should not be construed as a limitation. In an example, the neural network 1300 may be a convolutional neural network (CNN), recurrent neural network (RNN), long short-term memory (LSTM) based network, generative adversarial networks (GAN), or any combination thereof which may acts captured fluorescence data, such as the captured fluorescence data 218.

Although examples for the present disclosure have been described in language specific to structural features and/or methods, it is to be understood that the appended claims are not necessarily limited to the specific features or methods described. Rather, the specific features and methods are disclosed and explained as examples of the present disclosure.

We claim:

1. A system (202) for assessing susceptibility of a pathogen with respect to a target drug, the system (202) comprising:
   a processor (214);
   a detection engine (216) coupled to the processor, wherein the detection engine (216) is to:
      for a sample comprising a target pathogen and a predefined concentration of a target drug, determine autofluorescence features (220) based on autofluorescence exhibited by the sample in response to the sample being subjected to excitation radiation; and
      analyze the autofluorescence features (220) based on a machine-learning based susceptibility-detection model (110) to determine susceptibility of the target pathogen with respect to the target drug, wherein the susceptibility-detection model (110) is trained based on a training autofluorescence parameters (116) correlated with reference data (114), wherein the reference data (114) includes information pertaining to susceptibility or resistance of a reference pathogen with respect to a reference drug.

2. The system as claimed in claim 1, further comprising a plurality of light sources (210), wherein the plurality of light sources (210) are to generate the excitation radiation.

3. The system as claimed in claim 1, wherein the excitation radiation comprises radiation of a plurality of wavelengths within a range of about 200 nm to 600 nm.

4. The system as claimed in claim 1, wherein the excitation radiation comprises white light radiation.

5. The system as claimed in claim 4, wherein the detection engine (216) is to analyze reflectance parameters, transmittance parameters, or combination thereof, in response to excitation by white light radiation.

6. The system as claimed in claim 1, wherein to analyze the autofluorescence features (220) of the autofluorescence exhibited by the sample, the detection engine (216) is to:
   obtain captured images of the sample exhibiting autofluorescence;
   process the captured images to obtain autofluorescence features (220); and
   analyze the obtained susceptibility features based on the susceptibility detection model (110).

7. The system as claimed in claim 6, further comprising an image sensor, wherein the image sensor is to capture the images of the sample exhibiting autofluorescence.

8. The system as claimed in claim 6, comprising a detector (212), wherein the detector (212) is to detect fluorescence signals exhibited by a sample.

9. The system as claimed in claim 1, wherein the autofluorescence features (220) comprise fluorescence intensity, time dependent fluorescence parameters, amplitudes, and lifetimes.

10. A method training a susceptibility detection model (110) to be implemented in an assessment system for assessing susceptibility a target pathogen, the method comprising:
   obtaining reference data (114) pertaining to a set of reference pathogens, wherein the reference data (114) includes information pertaining to susceptibility or resistance of a reference pathogen with respect to a reference drug;
   obtaining training autofluorescence parameters (116) based on exhibited autofluorescence by the reference pathogen in the presence of a reference drug;
   correlating the reference data (114) and the training autofluorescence parameters (116) to provide the correlated information (118); and training a machine-learning based susceptibility detection model (110) based on the correlated information (118), wherein the susceptibility detection model (110) when implemented within the assessment system is to determine susceptibility of the target pathogen with respect to a target drug.

11. The method as claimed in claim 10, wherein the training autofluorescence parameters (116) may be determined based on spectral analysis of autofluorescence intensity at different spectral bands of autofluorescence emissions.

12. The method as claimed in claim 10, wherein the training autofluorescence parameters (116) are one of steady state autofluorescence parameters or time dependent parameters or a combination of both.

13. The method as claimed in claim 10, wherein the susceptibility detection model (110) is one of classification model, regression-based learning model, and a deep learning model.

14. The method as claimed in claim 10, wherein the pathogens may be one of a virus, bacteria, and fungi.

15. A non-transitory computer-readable medium comprising computer-readable instructions, which when executed by a processor of a computing device, cause the processor to:

subject a sample comprising a target pathogen and a predefined concentration of a target drug to excitation radiation;

determine fluorescence features (220) based on fluorescence exhibited by the sample in response to the sample being subjected to the excitation radiation; and analyze the fluorescence features (220) based on a machine-learning based susceptibility-detection model (110) to determine susceptibility of the target pathogen with respect to the target drug, wherein the susceptibility-detection model (110) is trained based on a training fluorescence features (116) correlated with reference data (114), wherein the reference data (114) includes information pertaining to susceptibility or resistance of a reference pathogen with respect to a reference drug.

16. The non-transitory computer-readable medium as claimed in claim 15, wherein the fluorescence is exhibited as a result of an exogenous fluorophores provided to the target pathogen.

17. The non-transitory computer-readable medium as claimed in claim 15, wherein the fluorescence exhibited is autofluorescence.

18. The non-transitory computer-readable medium as claimed in claim 15, wherein the excitation radiation comprises radiation of a plurality of wavelengths within a range of about 200 nm to 600 nm.

19. The non-transitory computer-readable medium as claimed in claim 15, wherein the instructions are to further generate a susceptibility indication (226) indicating whether the target pathogen is one of susceptible or resistant to the target drug.

20. The non-transitory computer-readable medium as claimed in claim 15, wherein to analyze the fluorescence features (220), the instructions when executed are to:

obtain captured images of the sample exhibiting fluorescence;

process the captured images to obtain fluorescence features (220); and analyze the obtained fluorescence features based on the susceptibility detection model (110).

\* \* \* \* \*